(12) United States Patent
Cuccia

(10) Patent No.: US 9,277,866 B2
(45) Date of Patent: Mar. 8, 2016

(54) METHOD AND APPARATUS FOR ANALYSIS OF TURBID MEDIA VIA SINGLE-ELEMENT DETECTION USING STRUCTURED ILLUMINATION

(71) Applicant: MODULATED IMAGING, INC., Irvine, CA (US)

(72) Inventor: David Cuccia, Costa Mesa, CA (US)

(73) Assignee: MODULATED IMAGING, INC., Irvine, CA (US)

(*) Notice: Subject to any disclaimer, the term of this patent is extended or adjusted under 35 U.S.C. 154(b) by 0 days.

(21) Appl. No.: 13/840,999

(22) Filed: Mar. 15, 2013

(65) Prior Publication Data

US 2013/0274612 A1 Oct. 17, 2013

Related U.S. Application Data

(62) Division of application No. 12/950,805, filed on Nov. 19, 2010.

(51) Int. Cl.
*A61B 5/00* (2006.01)

(52) U.S. Cl.
CPC .............. *A61B 5/0075* (2013.01); *A61B 5/0059* (2013.01)

(58) Field of Classification Search
CPC ........................... A61B 5/0073; A61B 5/0075
USPC .......................................................... 600/476
See application file for complete search history.

(56) References Cited

U.S. PATENT DOCUMENTS

| | | | |
|---|---|---|---|
| 4,286,602 | A | 9/1981 | Guy |
| 4,407,290 | A | 10/1983 | Wilber |
| 4,515,165 | A | 5/1985 | Carroll |
| 4,600,011 | A | 7/1986 | Watmough |
| 5,057,695 | A | 10/1991 | Hirao et al. |
| 5,140,463 | A | 8/1992 | Yoo et al. |
| 5,142,372 | A | 8/1992 | Alfano et al. |
| 5,203,339 | A | 4/1993 | Knüttel et al. |
| 5,227,912 | A | 7/1993 | Ho et al. |
| 5,275,168 | A | 1/1994 | Reintjes et al. |
| 5,277,181 | A | 1/1994 | Mendelson et al. |
| 5,299,035 | A | 3/1994 | Leith et al. |
| 5,349,951 | A | 9/1994 | Ito et al. |
| 5,353,799 | A | 10/1994 | Chance |

(Continued)

FOREIGN PATENT DOCUMENTS

| WO | WO 89/12223 A1 | 12/1989 |
|---|---|---|
| WO | WO 93/00045 A1 | 1/1993 |

(Continued)

OTHER PUBLICATIONS

Bélanger, Samuel, et al., "Real-time diffuse optical tomography based on structured illumination", Journal of Biomedical Optics, 15(1), 016006-1-016006-7 (2010).

(Continued)

*Primary Examiner* — Rajeev Siripurapu
(74) *Attorney, Agent, or Firm* — One LLP

(57) ABSTRACT

Method and apparatus for obtaining qualitative and quantitative analysis of the optical properties or structures of tissue or turbid medium at one or more wavelengths via 1) detection at a single spatial location on the surface of a turbid medium (such as tissue) under two or more structured light conditions or 2) detection at two or more spatial locations on the surface under a single structured light condition.

24 Claims, 9 Drawing Sheets

(56) References Cited

U.S. PATENT DOCUMENTS

| | | | |
|---|---|---|---|
| 5,369,496 A | 11/1994 | Alfano et al. | |
| 5,371,368 A | 12/1994 | Alfano et al. | |
| 5,416,582 A | 5/1995 | Knutson et al. | |
| 5,418,797 A | 5/1995 | Bashkansky et al. | |
| 5,625,458 A | 4/1997 | Alfano et al. | |
| 5,640,247 A | 6/1997 | Tsuchiya et al. | |
| 5,722,406 A | 3/1998 | Papaioannou | |
| 5,762,607 A | 6/1998 | Schotland et al. | |
| 5,865,754 A | 2/1999 | Sevick-Muraca et al. | |
| 5,903,357 A | 5/1999 | Colak | |
| 5,928,137 A | 7/1999 | Green | |
| 5,931,789 A | 8/1999 | Alfano et al. | |
| 5,969,822 A | 10/1999 | Fright et al. | |
| 5,987,351 A | 11/1999 | Chance | |
| 6,032,070 A | 2/2000 | Flock et al. | |
| 6,076,010 A | 6/2000 | Boas et al. | |
| 6,081,322 A | 6/2000 | Barbour | |
| 6,091,984 A | 7/2000 | Perelman et al. | |
| 6,104,946 A | 8/2000 | Tsuchiya et al. | |
| 6,108,576 A | 8/2000 | Alfano et al. | |
| 6,122,042 A | 9/2000 | Wunderman et al. | |
| 6,148,226 A | 11/2000 | Painchaud et al. | |
| 6,208,415 B1 | 3/2001 | De Boer et al. | |
| 6,208,886 B1 | 3/2001 | Alfano et al. | |
| 6,240,312 B1 | 5/2001 | Alfano et al. | |
| 6,321,111 B1 | 11/2001 | Perelman et al. | |
| 6,327,489 B1 | 12/2001 | Hoogenraad et al. | |
| 6,332,093 B1 | 12/2001 | Painchaud et al. | |
| 6,335,792 B1 | 1/2002 | Tsuchiya | |
| 6,348,942 B1 | 2/2002 | Watkins | |
| 6,399,935 B1* | 6/2002 | Jovin et al. | 250/216 |
| 6,404,497 B1 | 6/2002 | Backman et al. | |
| 6,405,069 B1 | 6/2002 | Oraevsky et al. | |
| 6,549,284 B1 | 4/2003 | Boas et al. | |
| 6,618,614 B1 | 9/2003 | Chance | |
| 6,624,890 B2 | 9/2003 | Backman et al. | |
| 6,678,541 B1 | 1/2004 | Durkin et al. | |
| 6,754,518 B1 | 6/2004 | Lloyd et al. | |
| 6,795,195 B1 | 9/2004 | Barbour et al. | |
| 6,825,928 B2 | 11/2004 | Liu et al. | |
| 6,922,583 B1 | 7/2005 | Perelman et al. | |
| RE38,800 E | 9/2005 | Barbour | |
| 6,958,815 B2 | 10/2005 | Bevilacqua et al. | |
| 7,046,832 B1 | 5/2006 | Barbour | |
| 7,139,603 B2 | 11/2006 | Chance | |
| 7,224,905 B2 | 5/2007 | Ruggiero | |
| 7,274,446 B2 | 9/2007 | Wolleschensky et al. | |
| 7,304,724 B2 | 12/2007 | Durkin et al. | |
| 7,428,434 B2 | 9/2008 | Tromberg et al. | |
| 7,610,082 B2 | 10/2009 | Chance | |
| 7,627,365 B2 | 12/2009 | Chance | |
| 7,637,893 B2 | 12/2009 | Christensen et al. | |
| 7,647,091 B2 | 1/2010 | Ntziachristos et al. | |
| 7,652,763 B2 | 1/2010 | Matousek et al. | |
| 7,692,160 B2 | 4/2010 | Lee et al. | |
| 7,717,888 B2 | 5/2010 | Vaillancourt et al. | |
| 7,729,750 B2 | 6/2010 | Tromberg et al. | |
| RE41,949 E | 11/2010 | Barbour et al. | |
| 7,873,407 B2 | 1/2011 | Levenson et al. | |
| 7,904,139 B2 | 3/2011 | Chance | |
| 7,911,604 B2 | 3/2011 | Matousek et al. | |
| 7,962,200 B2 | 6/2011 | Ntziachristos et al. | |
| 7,983,741 B2 | 7/2011 | Chance | |
| 8,014,569 B2 | 9/2011 | Durkin et al. | |
| 8,082,015 B2 | 12/2011 | Yodh et al. | |
| 8,085,396 B2 | 12/2011 | Matousek et al. | |
| 8,103,331 B2 | 1/2012 | Hoyt et al. | |
| 8,159,664 B2 | 4/2012 | Matousek et al. | |
| 8,170,651 B2 | 5/2012 | Ripoll Lorenzo et al. | |
| 8,185,176 B2 | 5/2012 | Mangat et al. | |
| D662,122 S | 6/2012 | Goodwin et al. | |
| 8,199,322 B2 | 6/2012 | Kashyap et al. | |
| 8,243,269 B2 | 8/2012 | Matousek et al. | |
| 8,259,902 B2 | 9/2012 | Matousek et al. | |
| 8,276,287 B2 | 10/2012 | Estocado | |
| 8,301,216 B2 | 10/2012 | Durkin et al. | |
| 8,310,532 B2 | 11/2012 | Mertz et al. | |
| 8,326,406 B2 | 12/2012 | Ntziachristos et al. | |
| 8,360,321 B2 | 1/2013 | Lee et al. | |
| 8,505,209 B2 | 8/2013 | Estocado | |
| 8,509,879 B2 | 8/2013 | Durkin et al. | |
| 8,606,032 B2 | 12/2013 | Nishi et al. | |
| 2003/0002028 A1 | 1/2003 | Rice et al. | |
| 2003/0184757 A1 | 10/2003 | Bevilacqua et al. | |
| 2004/0095576 A1 | 5/2004 | Wolleschensky | |
| 2006/0155195 A1 | 7/2006 | Maier et al. | |
| 2006/0173354 A1* | 8/2006 | Ntziachristos et al. | 600/476 |
| 2006/0184043 A1 | 8/2006 | Tromberg et al. | |
| 2006/0268241 A1 | 11/2006 | Watson et al. | |
| 2008/0101657 A1* | 5/2008 | Durkin et al. | 382/110 |
| 2009/0118622 A1 | 5/2009 | Durkin et al. | |
| 2010/0101069 A1 | 4/2010 | Christensen et al. | |
| 2010/0160754 A1 | 6/2010 | Durkin et al. | |
| 2010/0191321 A1 | 7/2010 | Schlun et al. | |
| 2010/0210931 A1 | 8/2010 | Cuccia et al. | |
| 2011/0124988 A1 | 5/2011 | Cuccia | |
| 2011/0149163 A1 | 6/2011 | Nishi et al. | |
| 2011/0284639 A1 | 11/2011 | Lee et al. | |
| 2012/0236310 A1 | 9/2012 | Lesage et al. | |
| 2013/0237841 A1 | 9/2013 | Freeman et al. | |
| 2013/0274612 A1 | 10/2013 | Cuccia | |
| 2013/0331708 A1 | 12/2013 | Estocado | |
| 2013/0345560 A1 | 12/2013 | Ferguson, Jr. et al. | |

FOREIGN PATENT DOCUMENTS

| | | |
|---|---|---|
| WO | WO 99/20997 A1 | 4/1999 |
| WO | WO 01/19241 A1 | 3/2001 |
| WO | WO 01/020546 A2 | 3/2001 |
| WO | WO 2004/069042 A2 | 8/2004 |
| WO | WO 2005/008195 A2 | 1/2005 |
| WO | WO 2006/061566 A1 | 6/2006 |
| WO | WO 2008/151159 A2 | 12/2008 |
| WO | WO 2011/035408 A1 | 3/2011 |

OTHER PUBLICATIONS

Bevilacqua, Frédéric, et al., "Broadband absorption spectroscopy in turbid media by combined frequency-domain and steady-state methods," Applied Optics, 39(34), pp. 6498-6507 (2000).

Cuccia, D. J., et al., "Quantitation and mapping of tissue optical properties using modulated imaging", Journal of Biomedical Optics, 14(2), pp. 024012-1-024012-13 (2009).

Gebhart, S. C., et al., "Liquid-crystal tunable filter spectral imaging for brain tumor demarcation", Applied Optics, 46(10), pp. 1896-1910 (2007).

Hale, G. M., et al., "Optical Constants of Water in the 200-nm to 200-μm Wavelength Region", Applied Optics, 12(3), pp. 555-563 (1973).

Haskell, R. C., et al., "Boundary conditions for the diffusion equation in radiative transfer", J. Opt. Soc. Am., 11(10), pp. 2727-2741 (1994).

Jacques, Steven L., "Melanosome absorption coefficient", retrieved from http://omlc.ogi.edu/spectra/melanin/mua.html, pp. 1-2 (1998).

Kobayashi, M., et al., "Analysis of nonlinear relation for skin hemoglobin imaging", Optics Express, 9(13), pp. 802-812 (2001).

Nishidate, Izumi, et al., "Estimation of melanin and hemoglobin in skin tissue using multiple regression analysis aided by Monte Carlo simulation", Journal of Biomedical Optics, 9(4), pp. 700-710 (2004).

Palmer, G. M., et al., "Monte Carlo-based inverse model for calculating tissue optical properties. Part I: Theory and validation on synthetic phantoms", Applied Optics, 45(5), pp. 1062-1071 (2006).

Prahl, Scott, "Optical Absorption of Hemoglobin", retrieved from http://omlc.ogi.edu/spectra/hemoglobin/index.html, pp. 1-3 (1999).

Rajaram, N., et al., "Lookup table-based inverse model for determining optical properties of turbid media", Journal of Biomedical Optics, 13(5), pp. 050501-1-050501-3 (2008).

Simpson, C. R., et al. "Near-infrared optical properties of ex vivo human skin and subcutaneous tissues measured using the Monte Carlo inversion technique", Phys. Med. Biol., 43, pp. 2465-2478 (1998).

(56) References Cited

OTHER PUBLICATIONS

Tseng, Sheng-Hao, et al., "In vivo determination of skin near-infrared optical properties using diffuse optical spectroscopy", Journal of Biomedical Optics, 13(1), pp. 014016-1-041016-7 (2008).

Van Staveren, H. J., et al., "Light scattering in Intralipid-10% in the wavelength range of 400-1100 nm", Applied Optics, 30(31), pp. 4507-4514 (1991).

Weber, J. R., et al., "Noncontact imaging of absorption and scattering in layered tissue using spatially modulated structured light", Journal of Applied Physics, 105, pp. 102028-1-102028-9 (2009).

"Wound imaging, measurement and healing progress documentation", retrieved from http://www.aranzmedical.com/wound-assessment/.

Blot, S. I., et al., "The Use of Laser Doppler Imaging in Measuring Wound-Healing Progress," Arch. Surg., vol. 136, p. 116 (2001).

Chen, M. H., et al., "Development of a Thermal and Hyperspectral Imaging System for Wound Characterization and Metabolic Correlation", Johns Hopkins APL Technical Digest, vol. 26, No. 1, pp. 67-74 (2005).

"Hyperspectral Imaging: Shedding New Light on Wound Healing", retrieved from http://www.nist.gov/pml/div685/hyperspectral.cfm.

Harper, J. R., "Wound Care: What's the Latest?", ACP/IMDA Scientific Meeting, pp. 1-59 (2011).

"Wound Image Analysis Guide for Clinicians", retrieved from www.InfoVACTherapy.com (2008).

Nourri, D., "Colour and multispectral imaging for wound healing evaluation in the context of a comparative preclinical study", published in Medical Imaging 2013: Image Processing, ake Buena Vista (Orlando Area), Florida: United States, pp. 1-10 (2013).

"SPY Imaging in the Treatment of Non-healing Wounds", retrieved from http://www.novadaq.com/procedures/wound-care.

"LUNA Flourescence Angiography for Wound Care", retrieved from http://www.novadaq.com/products/luna-flourescence-angiography.

Salcido, R., "Beyond Photography: Wound Imaging", Skin and Wound Care, vol. 24, No. 2, p. 56 (2011).

Dargaville, T. R., et al. "Sensors and Imaging for Wound Healing: A Review", Biosensors and Bioelectronics, vol. 41, pp. 30-42 (2013).

"Scout", retrieved from http://www.woundvision/scout/.

Yudovsky, D., et al. "Hyperspectral Imaging in Diabetic Foot Wound Care", Journal of Diabetes Science and Technology, vol. 4, No. 5, pp. 1099-1113 (2010).

Zhou, A. H., "A Survey of Optical Imaging Techniques for Assessing Wound Healing", Intl. Journal of Intelligent Control and Systems, vol. 17, No. 3, pp. 79-85 (2012).

\* cited by examiner

METHOD AND APPARATUS FOR ANALYSIS OF TURBID MEDIA VIA SINGLE-ELEMENT DETECTION USING STRUCTURED ILLUMINATION

CROSS-REFERENCE OF RELATED APPLICATION

This application is a Divisional of application Ser. No. 12/950,805, filed Nov. 19, 2010.

FIELD

The embodiments described herein relate generally to optical measurement of turbid media and in particular to optical measurement of tissue absorption and scattering parameters via a single-element detector using one or more structured illuminations.

BACKGROUND

There has been considerable research in the use of near-infrared optical spectroscopy (NIRS) as a means for real-time in-vivo measurements of tissue optical properties which contain information on tissue structure and function. In the 600-1000 nm spectral region in particular, tissue is scattering dominated and the strongest molecular absorbers in tissue are oxygenated and deoxygenated hemoglobin, water, and lipids. The highly diffusive photons probe a large sample volume, providing macroscopically averaged absorption and scattering properties at depths up to a few centimeters.

The amount of light reflected or transmitted from tissues is due to a complex combination of absorption, scattering and (typically very weak) fluorescence. In order to measure any of these optical properties of a given sample, one has to first separate/isolate the absorption effects from scattering effects. Possession of this capability is enabling for a wide range of medical (diagnostic, therapeutic monitoring, cosmetic) and non-medical applications (material inspection, visualization, photo-realistic rendering, agricultural inspection, chemical slurry and powder analysis).

NIR techniques (though actually not limited to the NIR spectral range) combine experimental measurements and model-based data analysis to quantitatively measure the bulk absorption ($\mu_a$) and scattering ($\mu_s'$) properties of the tissue. Once $\mu_a$ and $\mu_s'$ are known at a variety of wavelengths, the concentration of the various molecular absorbers can be determined.

Several techniques have been developed over the last decade to measure tissue properties in vivo, and they can be broadly grouped into two categories: (1) photon migration techniques and (2) optical biopsy techniques. Most instruments of these types rely on a fiber optic contact probe measurement so that the source-detection geometry is well defined. The geometry allows for the quantitative measurement of absorption and scattering properties of the tissue, but it is limited to a single, small area. Photon migration instruments usually use source-detector separations of a few centimeters, resulting in spatial resolutions on the order of one centimeter, such that $\mu_a$ and $\mu_s'$ can be determined for thick tissue, such as breast, brain and muscle. Optical biopsy techniques usually use source-detector distances on the order of 100's of microns, thus they interrogate a smaller spatial scale that is typically on the order of one millimeter.

For many medical diagnostic applications, there is need for techniques that combine some of the physiological information that photon migration and optical biopsy provide, but have a wide field, non-contact imaging capability. Multispectral imaging systems that use a camera with a tunable spectral light source (or spectral detection filters) have been used in this capacity. There is a fundamental issue, however, on the inability of camera systems to distinguish between light that is absorbed by the tissue and light that is scattered. Imaging systems that use full-field illumination (i.e. flash photography) cannot differentiate between the two effects and assumptions are made in order to provide "quantitative" biochemical analysis. In practice, this deficiency results in qualitative analysis that depicts relative concentration changes within an image.

A more detailed discussion of these techniques is provided in Cuccia. *Modulated Imaging: A Spatial Frequency Domain Imaging Method for Wide-field Spectroscopy and Tomography of Turbid Media*, Ph.D. Dissertation, University of California, Irvine, Dept. of Biomedical Engineering("Cuccia, Modulated Imaging"); and Cuccia, et al., *Quantitation and mapping of tissue optical properties using modulated imaging*, J Biomed Opt 14(2), 024012 (2009) ("Cuccia, Quantitation and mapping").

Due to the deficiencies of prior techniques, a technique and technology platform, referred to as "Modulated Imaging" (MI), was developed. The key aspect of this type of imaging is that the absorption and scattering components are separated and used to evaluate tissue structure and calculate quantitative biochemical maps. The MI method uses structured light projection and camera-based detection in order to obtain quantitative measurements of:

1. sub-surface tissue optical properties, including:
   a. tissue absorption due to:
      i. endogenous chromophores such as oxy- and deoxy-hemoglobin, water, lipids, melanin, bilirubin, porphyrins, etc. and
      ii. exogenous dyes such as indocyanine green, methylene blue, synthetic agents, etc.
   b. tissue fluorescence/phosphorescence due to subsequent remission of light after absorption from a molecule above
   c. tissue scattering, (microscopic refraction) including both scattering magnitude and direction, due to:
      i. cellular structures such as nuclei, mitochondria, cell membranes,
      ii. extracellular structures, such as collagen
      iii. exogenous agents
2. surface profile information (profilometry)

A detailed description of the MI method including spatial frequency domain imaging (SFOI) measurement, calibration, and analysis has been previously reported in Cuccia, *Quantitation and mapping*, and U.S. Pat. No. 6,958,815, which are incorporated herein by reference.

From an apparatus perspective, an innovative aspect of MI/SFDI is its combination of a camera and a structured light projection system that allows one to reconstruct quantitative maps in 20 or 30 of tissue optical properties. Structured light illumination, also commonly referred to as spatially structured illumination, includes, among other, such illumination as sinusoidal illumination and periodic illumination. Generally, the structured illumination patterns give multiple "views" into the tissue and reveal the contrast between various structures and optical properties that would otherwise be obscured or mixed together. The system is typically non-contact, allowing for easy use in applications including surgical guidance where the tissue of interest can be interrogated without contamination.

From a method perspective, the camera images can be analyzed in a variety of ways to extract this quantitative information. The most common embodiment is "spatial frequency domain" analysis, involving either 1) processing a single Fourier-transform of the images, or 2) by directly manipulating a series of images under multiple structured illumination conditions—typically a spatial sine wave at various spatial phases. A strong benefit to methods that use approach 2) above is that they lend themselves more readily toward recovering high-resolution maps (in 2D or 3D) of the recovered properties, thus allowing for spatially-resolving structures and/or determining the depth of various structures/layers/etc.

Another innovation aspect of MI is the combination of simultaneous profile measurements along with tissue optical property determination. Profilometry is commonplace in areas such as machine vision and cosmetic dermatology.

As stated above, MI has the unique capability of spatially resolving optical absorption and scattering parameters, allowing wide-field quantitative mapping of tissue optical properties with the use of spatially-modulated illumination. FIG. 1 shows the configuration of a laboratory-grade system 10. Light from a halogen lamp 11 is expanded by a condenser 12 onto a spatial light modulator (SLM) 15. The current system uses a Digital Micromirror Device (DMD) from Texas Instruments which is a 1024×768 mirror array that can generate and project arbitrary grayscale patterns. Such patterns are directed through a projector lens 16 and reflected off a mirror 17 to the surface of the tissue T and the diffusely reflected light is then recorded by a digital CCD camera 19. In the laboratory instrument, a filter wheel 13 was used to interrogate a discrete number of wavelengths. Instead of a filter wheel, a tunable filter or tunable spectral source can be used to interrogate a discrete number of wavelengths. Crossed linear polarizers 14 and 18 can be introduced into the source and detection light paths to remove specular reflectance. The SLM 15, camera 19 and spectral device are synchronized with a computer and/or trigger board, enabling fast acquisition of a series of patterns at various spatial frequencies. A turbid reflectance standard (such as a Ti02-based silicone phantom) can be used to calibrate the source intensity and to correct for spatial non-uniformities in both the illumination and imaging systems.

Periodic illumination patterns of various spatial frequencies are projected over a large (many cm$^2$) area of a sample. Typically, sine-wave illumination patterns are used. The reflected image captured by the camera differs from the illumination patterns due to the optical property characteristics of the sample. The demodulation of these spatially-modulated waves characterizes the sample modulation transfer function (MTF), which embodies the optical property information of the tissue.

For example, the tissue can be illuminated with a spatial pattern of the form:

$$S = \frac{S_O}{2}[1 + M_0\cos(2\pi f x + a)] \quad (1)$$

where $S_0$, $M_0$, $f_x$ and a are the illumination source intensity, modulation depth, spatial frequency, and spatial phase, respectively. The diffusely reflected intensity, I, is a sum of the spatially-varying (AC) and spatially-constant (DC) components of the illumination signal. These AC and DC spatial components do not relate to other uses of the terms AC and DC, such as the AC and DC components of electrical signals, or the AC and DC temporal components, for example those delineated in Sevick-Muraca U.S. Pat. No. 5,865,754. The underlying physics, detection schemes, analysis methods and mathematical models aimed at characterizing these AC and DC spatial components are all distinct from other uses of these terms.

The top row of images, shown in FIG. 2, show the images obtained for illumination patterns at four spatial frequencies (with only 1 phase of each frequency shown). The AC component of the reflected intensity, /Ac, can be modeled as:

$$I_{AC} = M_{AC}(x, f_x) \cdot \cos(2\pi f_x + \alpha)$$

Here, MAc(xJx) represents the amplitude of the reflected photon density "standing wave" at frequency fx. Note that MAc can be a function of position, x. To obtain MAc(xJx), a simple time domain amplitude demodulation method is employed, illuminating a sinusoid pattern three times at the same spatial frequency, with phase offsets a=0, 2/3 n and 4/3 n radians. MAc(xJx) can then be calculated algebraically at each spatial location, xi, by:

$$M_{AC}(x, f_x) = [(I_1 - I_2)^2 + (I_2 - I_3) + (I_3 - I_1)]^{1/2} \quad (3)$$

The spatially-varying DC amplitude, Moc(x), can be calculated using:

$$Moc(X, f x) = [/1 + !2 + /3]/3 \quad (4)$$

where 11, 12, and /3 represent the /Ac image values at each location with shifted spatial phases.

Finally, measurement of a reference turbid phantom of known optical properties allows model-based calibration for the source intensity, $S_0$, and therefore conversion of MAc and Moc to calibrated diffuse reflectance, RAc and Roe, respectively. Once the AC and DC components of the reflectivity are determined, a "White Monte Carlo" (WMC) method is used to provide accurate and rapid models of predicting light transport over a wide range of reflectivities. At each wavelength, the spatial-frequency-dependent diffuse reflectance is fitted to WMC forward predictions for every pixel in the image and obtain the µa and µs' optical properties, as shown at the bottom of FIG. 2. This can be performed with a rapid two-frequency lookup table using a minimal 3-phase, single frequency image set (by demodulating and averaging the images to obtain AC and DC amplitude maps, respectively). This simple algorithm can easily be implemented for real-time processing and/or implementation on camera FPGA hardware. Alternatively, this analysis could be performed via other predictive, statistical, or heuristic models.

By mapping the absorption coefficient at multiple wavelengths, quantitative spectroscopy of tissue can optionally be performed. The result is a 3D data cube with an absorption spectrum at each spatial location. Knowledge of the extinction coefficients of the tissue chromophores (e.g. oxy- and deoxy-hemoglobin, lipids, water, etc) allows these spectra to be fitted to a linear Beer-Lambert absorption model and determine the quantitative concentrations of each chromophore.

Any of the aforementioned point detection systems, measurements, and analyses could be further spatially multiplexed to yield 1D, 2D, or 3D spatial representations of the turbid medium optical properties and/or structures. From a hardware standpoint, this would include multiple copies of a previously described detector setup, or an optical relay or scanning system to relay detector information from various locations on the sample.

As described above, the generally regarded innovative aspect of MI is the combination of a camera (2D light sensor) and a structured illumination system (2D projector) to enable the measurement and 2D/3D mapping of optical properties and tissue structures. Although this system can be constructed with consumer-grade electronics, it nevertheless requires a certain level of cost and complexity due to the presence of a 2D sensor. For example, when the method is extended for spectroscopy (measurement of multiple wavelengths), it adds significant system complexity and/or measurement time constraints, requiring either serial single-wavelength measurements or bulky and expensive multi-spectral imaging systems. In addition, although combination/integration with measurement methods that use time-modulation of light is also theoretically possible (in addition to spatial structuring or spatial modulation of light), this has never been feasible or desirable as it requires expensive, bulky, and low-fidelity time gating systems for cameras.

Thus, it is desirable to provide a less costly and complex system to analyze the optical properties and structures of turbid media.

BRIEF DESCRIPTION OF THE DRAWINGS

The details of the example embodiments, including structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

It should be noted that elements of similar structures or functions are generally represented by like reference numerals for illustrative purpose throughout the figures. It should also be noted that the figures are only intended to facilitate the description of the preferred embodiments.

DESCRIPTION

The various embodiments and examples provided herein are generally directed to a method and apparatus for obtaining qualitative and quantitative analysis of the optical properties or structures of tissue or turbid medium via detection via a single-element detector at a single spatial location or defined collection area on the surface of a turbid medium (such as tissue) under two or more structured light conditions or illuminations. The single spatial location or defined collection area is a localized spot or region and is preferably sized or dimensioned on the order of a feature of the illumination function. The signal detected on the single-element detector comprises a combination of the signals from all points within the single spatial location or defined collection area, wherein the single spatial location or defined collection area comprises one or more points.

Alternatively, detection is accomplished via a single-element detector at two or more spatial locations or defined collection areas on the surface of tissue or other turbid medium under a single structured light condition or illumination. Instead of focusing on a single spatial location or defined collection area that is subject to two or more structured light conditions or illuminations, two or more single-element detectors focus on two or more spatially diverse locations or defined collection areas allowing for the detection of differing structured light conditions or illuminations without modifying the source of structured light or illumination.

In the single-element detection methods noted above, detection can be implemented a) with a single-element detector/sensor in contact with the surface of the tissue or other turbid medium or b) otherwise delivered to a single-element detector via a fiber optic or lens relay system. The structured illumination can be implemented in contact form (via an LCD, LED array, or filtered backlight, for example) or non-contact form (via a slide projector, DMD/OLP, LCOS, or coherent interference, for example). In a preferred embodiment the structured illumination is spatially structured, but could alternatively be spectrally structured (changing the wavelength-dependent source intensity) to reveal optical properties and structures. Diagrams of these modes of operation are given in FIGS. 3A-3D.

Figure 1:
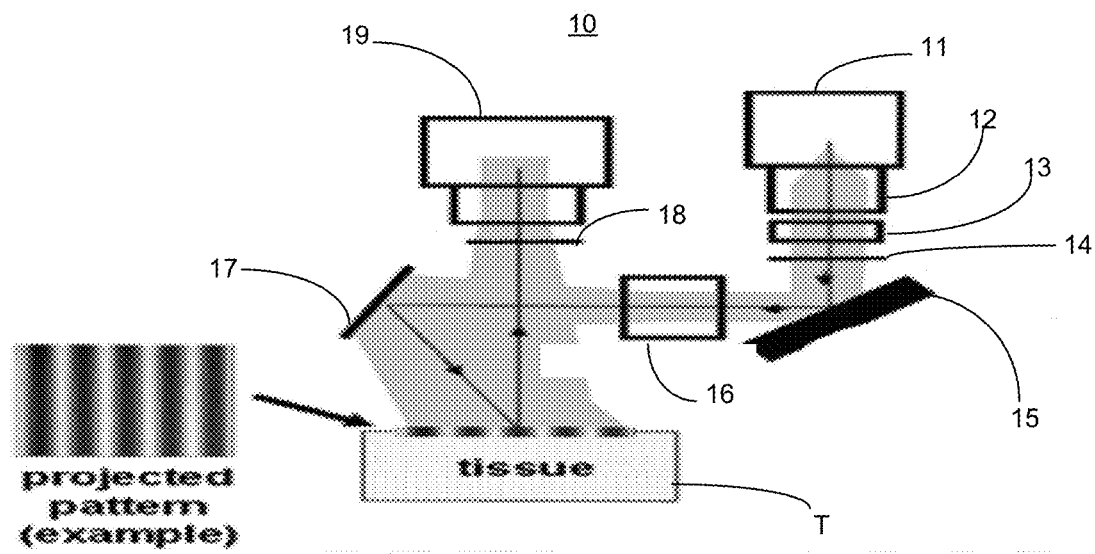
FIG. 1 is a schematic of a conventional modulated imaging system.
Figure 2:
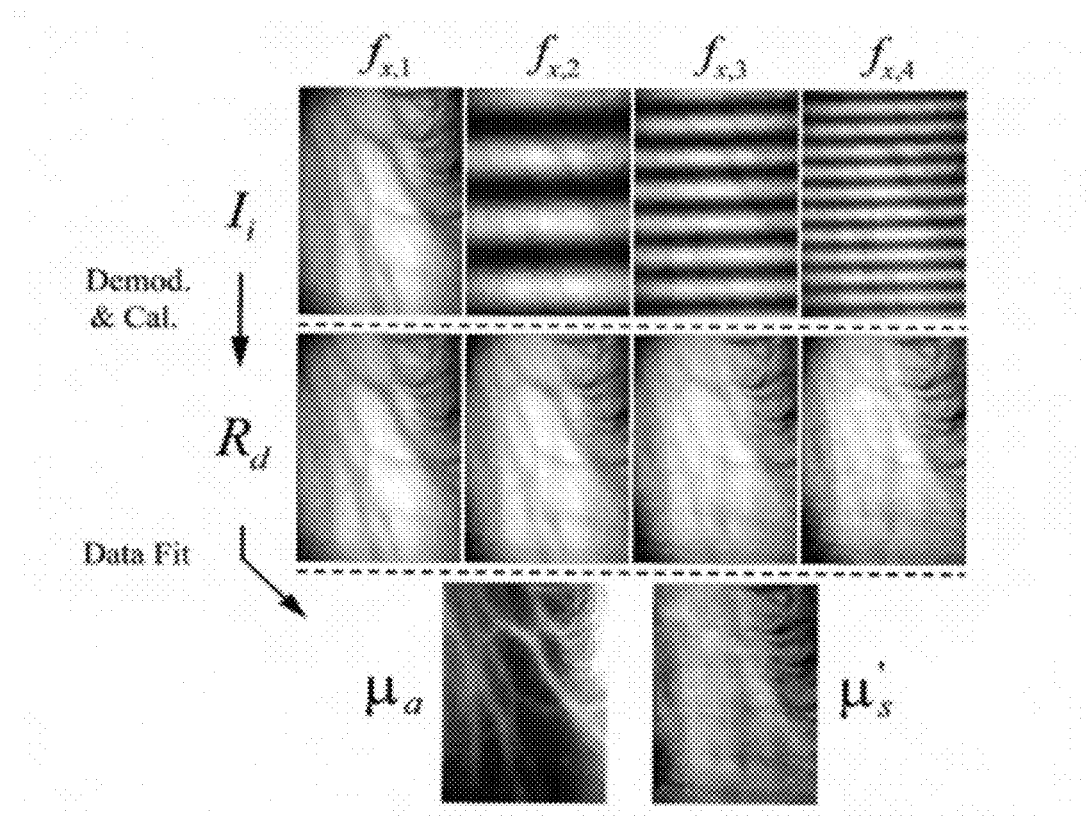
FIG. 2 is a flow diagram of the data analysis flow of the modulated imaging technique.
Figure 3A:
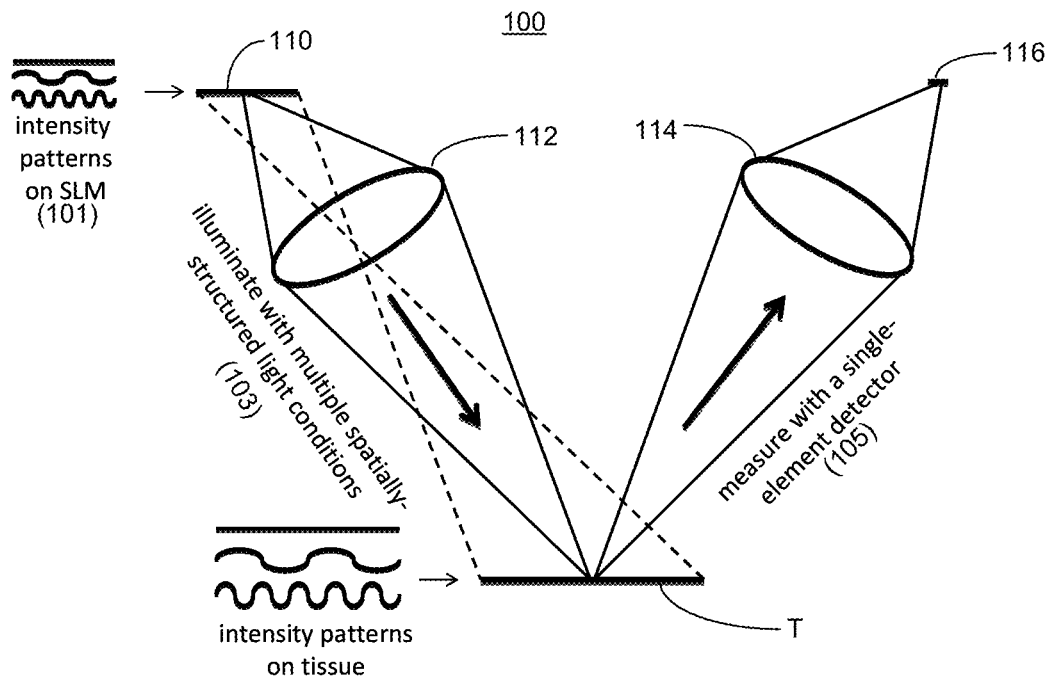
FIG. 3(a) is a schematic of a single-element detector and intensity-modulated source in space.
Figure 3B:
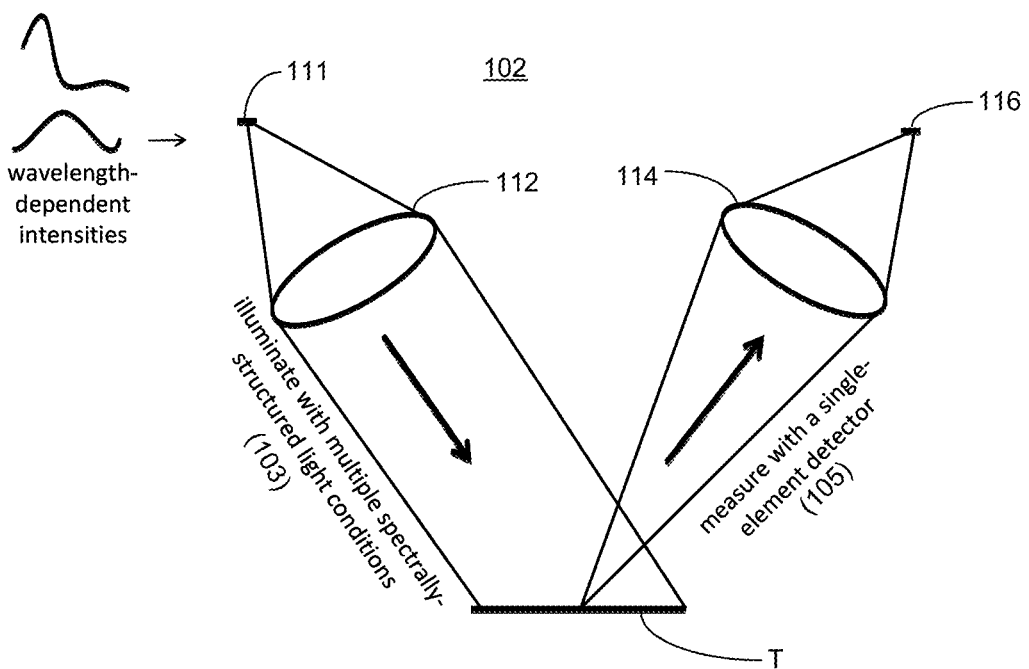
FIG. 3(b) is a schematic of a single-element detector and intensity-modulated source in wavelength.

Turning to FIG. 3A, a method and apparatus 100 is depicted for single element detection using multiple spatially structured illuminations. At step (101), multiple structured light patterns are generated by a spatial light modulator (SLM) 110. Next, at step (103) spatially structured light conditions are projected through a projection lens, a generalized relay, or a contact illumination system 112 onto the surface of the target medium T comprising tissue or other turbid medium to illuminate the target medium T with multiple spatially-structured light conditions. At step (105), light remitted, i.e., diffusely reflected or transmitted, from a single spatial location on the surface of the target medium T is coupled to a single-element detector 116 through a detector lens, a generalized relay, or a contact detection system 114.

Figure 3C:
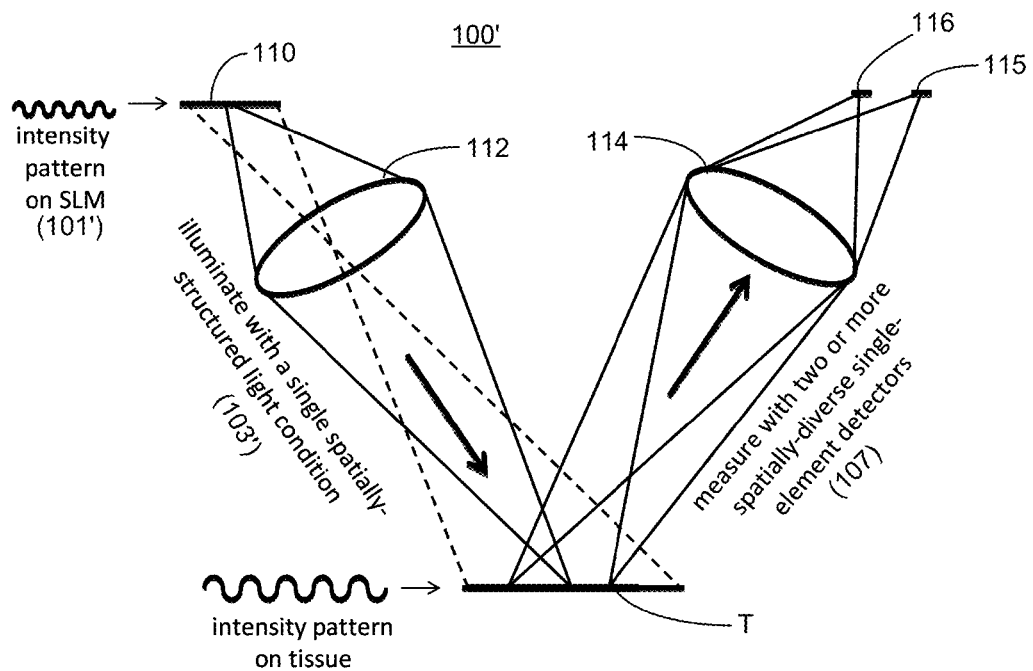
FIG. 3(c) is a schematic of single-element detection at two locations under one spatially-structured condition.
Figure 3D:
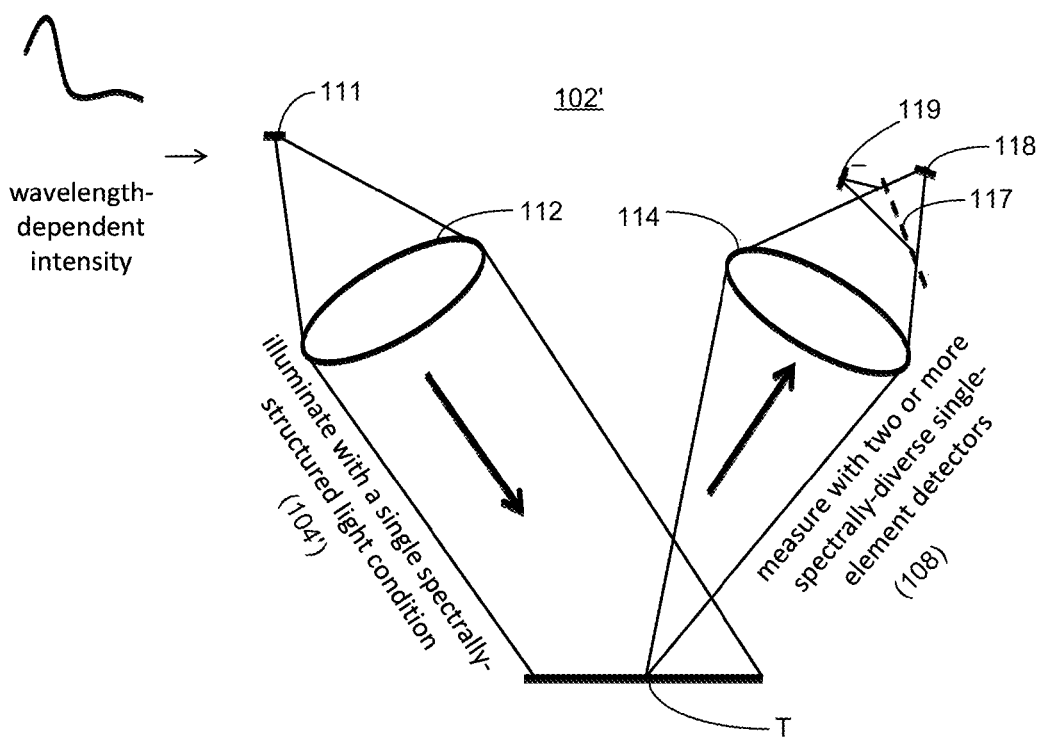
FIG. 3(d) is a schematic of single-element detection under two spectrally-diverse single-element detectors under a single spectrally-structured illumination condition.

Instead of using multiple spatially-structured light patterns, FIG. 3C depicts a method and apparatus 100' for single element detection using a single spatially structured illumination and one or more single element detectors. At step (101'), a single structured light pattern is generated by a spatial light modulator (SLM) 110. Next, at step (103') a spatially-structured light condition is projected through a projection lens, a generalized relay, or a contact illumination system 112 onto the surface of the target medium T to illuminate the target medium T with a single spatially-structured light condition. At step (107), light remitted from two or more spatially diverse locations on the surface of the target medium Tis coupled through a detector lens, a generalized relay, or a contact detection system 114 to two or more spatially diverse single-element detectors 115 and 116, or to one single-element detector 116 that is moveable or able to be oriented in two or more configurations or spatially diverse locations to detect the light remitted from the two or more spatially diverse locations on the surface of the target medium T.

Alternatively, FIG. 38 depicts a method and apparatus 102 for single element detection using multiple spectrally-structured illuminations. At step (104), multiple spectrally-structured light conditions generated by a variable multi-spectral light source 111 are projected through an illumination lens, a generalized relay, or a contact illumination system 112 onto the surface of the target medium T to illuminate the target medium T with multiple spectrally-structured light conditions. At step (105), light remitted from the surface of the target medium Tis coupled to a single-element detector 116 through a detector lens, a generalized relay, or a contact detection system 114.

Instead of using multiple spectrally-structured light patterns, FIG. 30 depicts a method and apparatus 102' for single element detection using a single spectrally-structured illumination and two or more single element detectors. At step (104'), a single spectrally structured light condition generated by a variable multi-spectral light source 111 is projected through an illumination lens, a generalized relay, or a contact illumination system 112 onto the surface of the target medium T to illuminate the target medium T with a single spectrally-structured light condition. At step (108), two or more spectrally diverse light signals remitted from the surface of the target medium Tare coupled through a detector lens, a generalized relay, or a contact detection system 114 and beam splitter, spectrometer, or other spectral selection device 117 to two or more spectrally diverse single-element detectors 118 and 119.

Figure 4:
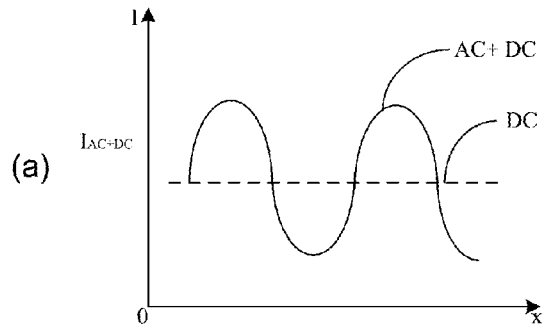
FIGS. 4(a)-4(d) are illumination and reflectance graphs of a single-element detection method utilizing two illuminations and one detector.
Figure 4:
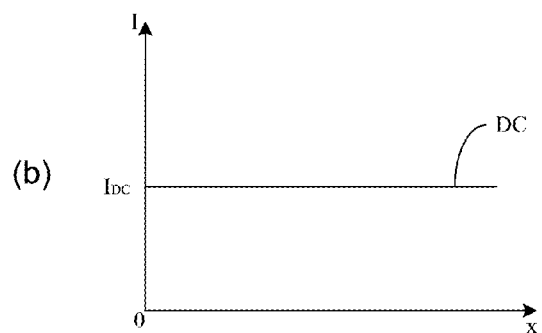
Figure 4:
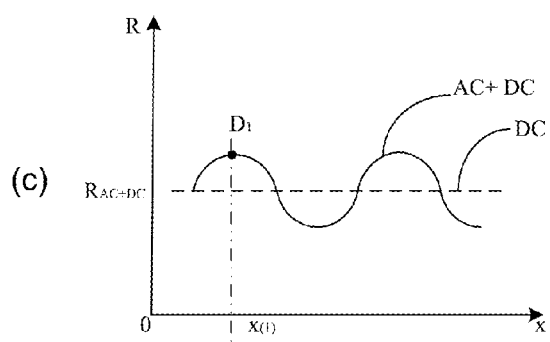
Figure 4:
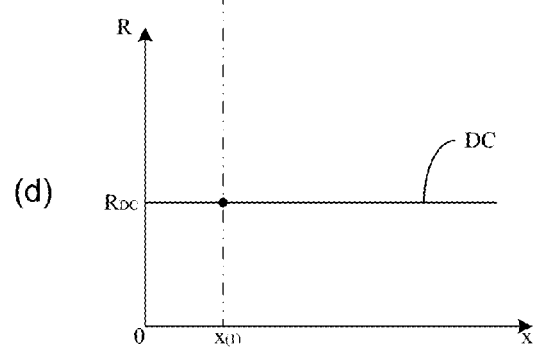

Turning to FIGS. 4(a)-4(d), a single-element detection method is depicted using one detector and two structured illuminations. As depicted in FIG. 4(a), the first illumination, IAe+oe, comprises a sinusoidal waveform, IAe, with a constant offset, Ioe. The second illumination, $1_0$e, shown in FIG. 4(b), comprises an illumination having a spatially constant intensity equivalent to the constant offset, Ioe, of the first illumination, IAe+oe. The magnitude of the remitted light corresponding to the first illumination, IAe+oe, and detected by a single-element detector at point x(1| on the surface of the illuminated tissue or other turbid medium is depicted as RAe+oe in FIG. 4(c). The magnitude of the remitted light corresponding to the second illumination, $1_0$e, and detected by a single-element detector at point x(1| on the surface of the illuminated tissue or other turbid medium is depicted for the as Roe in FIG. 4(d). Although shown as a point, i.e., x(1), the single spatial region from which signals are collected cannot in practice be an infinitesimally small point location but rather is a localized spot or region. The magnitude of the reflected light detected by the single-element detector resulting from only the AC component of the first structured illumination is determinable from: RAe=RAe+oe−Roe.

Figure 5:
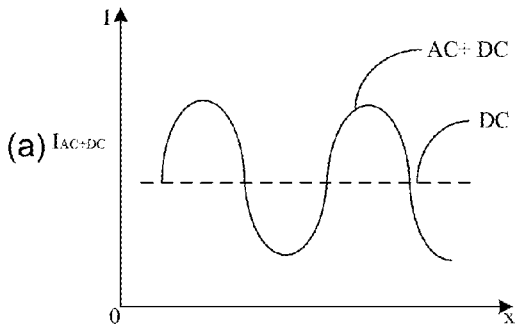
FIGS. 5(a)-5(b) are illumination and reflectance graphs of a single-element detection method utilizing one illumination and two detectors.
Figure 5:
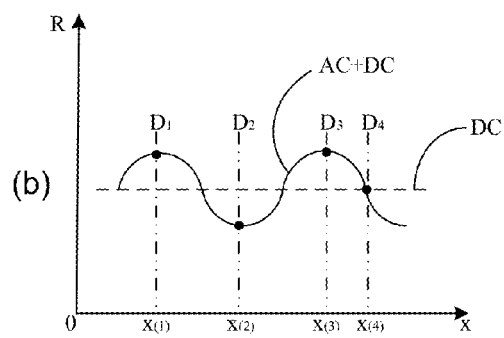

Alternatively, FIGS. 5(a)-5(b) depicts a single-element detection method using two spatially diverse detectors and one structured illumination. As depicted in FIG. 5(a), the structured illumination, IAe+oe, comprises a sinusoidal waveform, IAe, with a constant offset, $1_0$e. The magnitude of the remitted light corresponding to the AC and DC components of the structured illumination that is detected by first and second single-element detectors at a first location x(1| and a second location x(2| on the surface of the illuminated tissue or other turbid medium, as depicted in FIG. 5(b), is determinable from: Roe=(Rx(1)+Rx(2J)/2; RAe=(Rx(1)−Rx(2J)/2. The magnitude of remitted light corresponding to the AC and DC components of the structured illumination that is detected by first and second single-element detectors at a third location x(3| and a fourth location x(4| on the surface of the illuminated tissue or other turbid medium, is determinable from: Roe=Rx(4); RAe=Rx(3)−Rx(4).

Figure 6:
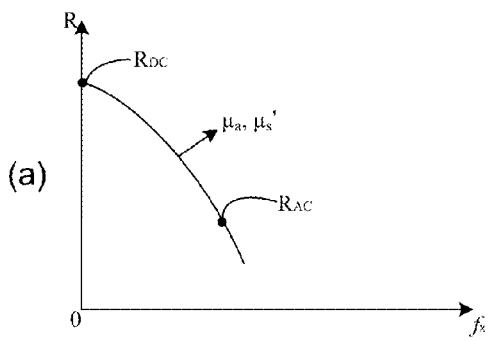
FIGS. 6(a)-6(b) are graphs of bulk absorption ($\mu a$) and scattering ($\mu s'$) as a function of the AC and DC reflectance components.
Figure 6:
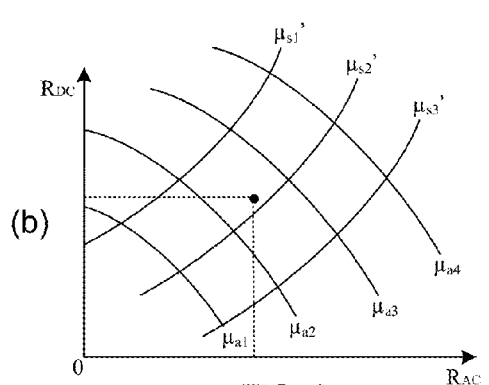

As shown in FIGS. 6(a) and 6(b), the values of Roe and RAe can be used to determine the bulk absorption ($\mu$a) and scattering ($\mu$s') properties of the tissue or other turbid medium. For example, as depicted in FIG. 6(b), an experimental or model generated look-up table can be used to determine the bulk absorption ($\mu$a) and scattering ($\mu$s') properties of the tissue or other turbid medium.

In some embodiments of single-element detection methods, it may be advantageous to allow the light collected by the single-element detector to be larger than a single "point" location or localized area so that instead of collecting light from a single "point" location, light is collected from a collection of points simultaneously where the signal detected on the single-element detector would be a combination of the signals from all the points included in a de-localized defined collection area. The defined collection area can be on the order of or larger than a feature of the illumination function. Measurement or detection of light collected from such a defined collection area could be accomplished simply by defocusing of a detection lens, or otherwise allowing the detector aperture to collect light from a larger area of the sample surface. In the same manner as before, the spatial content of the source-detector configuration would be designed to isolate the desired information content within the tissue or other turbid medium. The data from this approach would be treated in a similar fashion as with previously described source-detector configurations, including post-processing, filtering, calibration, model-based or lookup-table based calculations. Finally, this concept of de-localization in space can just as easily be applied to localization in wavelength spectrum, as it applies to the previously-described spectral modulation schemes.

Figure 7:
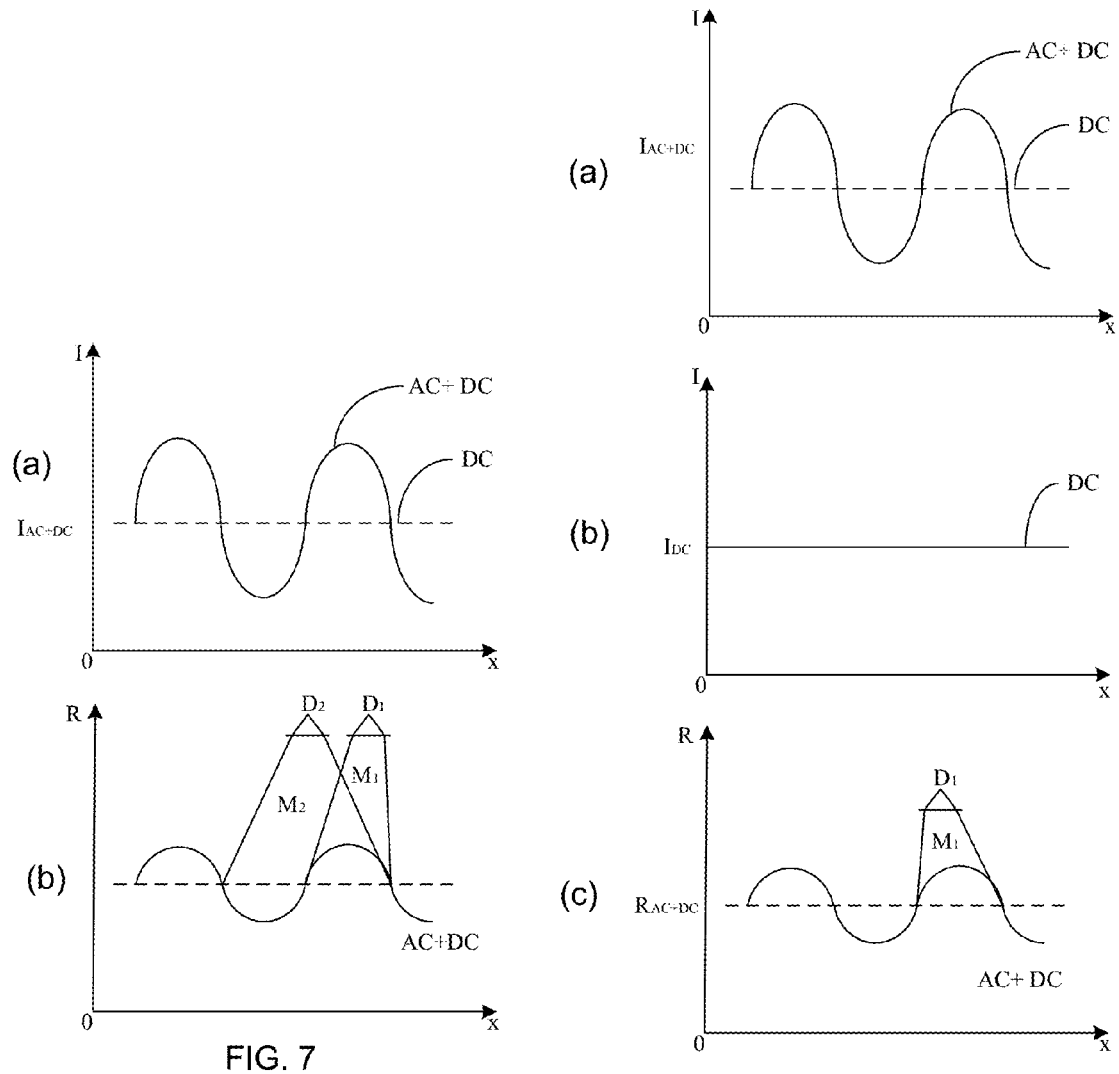
FIGS. 7(a)-7(b) are illumination and reflectance graphs of a single-element detection method utilizing one illumination and two detectors.
Figure 8:
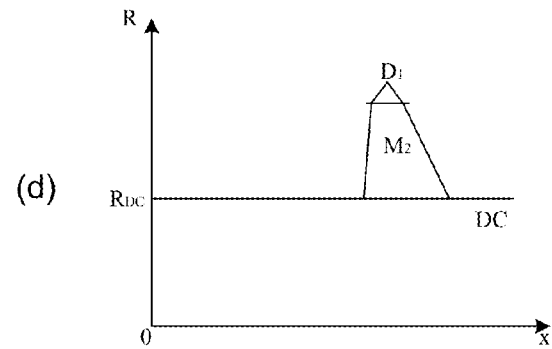
FIGS. 8(a)-8(d) are illumination and reflectance graphs of a single-element detection method utilizing two illuminations and one detector.

Turning to FIGS. 7(a) and (b), a single-element detection method utilizing a de-localized defined collection area is shown. A single periodic function, IAc, in x (such as a sine wave) is illuminated with a constant offset, $1_0$c. For example, the illumination could be in the form I1ota1=cos(k*x)+Ioc, where x is the lateral spatial dimension and k is the spatial frequency. The reflectance or transmittance is measured by single-element detectors 01 and 02 with two differing area-collection schemes. For example, the detector 01 could be designed to collect information over a half-integer-multiple (0.5, 1.5, 2.5, etc) of the illumination function spatial period and produce a magnitude measurement $M_1$. The detector 02 could be designed to collect information over an integer-multiple (1, 2, 3, etc) period of the periodic illumination, producing magnitude measurement $M_2$. As the measurement $M_2$ was performed over integer-multiples of the illumination period, the AC component would cancel, giving Roe=$M_2$. However, $M_1$ contains both AC contrast in addition to DC information and could be used to calculate the AC reflectance component. If the integer multiple was the same for both conditions, then M1 and M2 would differ by just a half-period and RAe=IMrM1I–

In the alternative, as shown in FIGS. 8(a)-8(d), the tissue or other turbid medium is illuminated with a periodic function, IAe, in x (such as a sine wave) with a constant offset, $1_0$e. For example, the periodic function illumination with constant offset could be in the form I1ota1=cos(k*x)+Ioe, where x is the lateral spatial dimension and k is the spatial frequency. The tissue or other turbid medium is also illuminated with an illumination having a spatially constant intensity, $1_0$e. The reflectance or transmittance is measured by one single-element detector 01 with the same area-collection scheme. For example, the detector 01 could be designed to collect information over a half-integer-multiple (0.5, 1.5, 2.5, etc) of the illumination function spatial period and produce magnitude measurement $M_1$ for the reflectance or transmittance corresponding to the periodic function illumination with constant offset, I1ota1=cos(k*x)+Ioe. For the reflectance or transmittance corresponding to the illumination having a spatially constant intensity, $1_0$e, the detector 01 produces a magnitude measurement $M_2$. As measurement $M_2$ was performed on the remittance due to the spatially constant illumination, there is no AC component and, thus, gives Roe=$M_2$. $M_1$ contains both AC contrast in addition to DC information and could be used to calculate the AC reflectance component where RAe=IMrM1I–

In more complex scenarios, detecting light from arbitrarily complex area functions designed to reveal the desired sample properties or structures, such as separately isolating remitted light from the crests and valleys of a periodic illumination function, producing measurements M1 and M2. In this case Roe=M1+M2 and RAe=IMrM1I–

In another example, a Bessel function plus some constant offset, $1_0$e, is illuminated where the total illumination is I1ota1=Jo(k*x)+Ioe, where Jo is a Bessel function of order zero, x is the spatial (lateral) position and k is the lateral spatial frequency, and detect (with a single-element detector) the total light remitting or transmitting from positions x=O to Xmax. This magnitude measurement is referred to as $M_1$. Separately, one could illuminate with a spatially-constant intensity, $1_0$e, only, thus detecting a different magnitude, $M_2$ with the same detector configuration. These magnitudes $M_1$ and $M_2$ alone would be sufficient for calculating optical properties and/or locating structures (in a similar fashion as with previously described source-detector orientations), even though they have not isolated a single spatial feature of the illumination beam (e.g. a crest or peak of the sine wave). For example, if $M_1$ and $M_2$ are the magnitudes of the measurements made by the first and second illumination conditions, and the maximum radius of detection Xmax was set to a "zero" of the illumination Bessel function, then a magnitude estimate for DC and AC components of the reflectance, Roe and RAe respectively, would be Roe=M2 and RAe=M1–M2. It has been previously shown how a minimum measurement Roe and RAe are sufficient for calculating optical properties, such as the absorption and reduced scattering coefficients, μa and μs', respectively.

The advantage of the single element detection methods described herein is primarily in the single element detector aspect of the apparatus. The instrument measurement, calibration, and analysis methods can optionally be practiced as described above with regard to the MI method and further expanded upon in Cuccia, *Modulated Imaging*, Cuccia, *Quantitation and mapping*, and U.S. Pat. No. 6,958,815, which are incorporated herein by reference, except that 1) the detector is a (a) single-element sensor or other optical detector, or (b) the entrance pupil for an optical relay device (such as the face of an optical fiber, for example), or (c) other point or localized area detection system, and 2) there is no spatial dependence to the detected signal the 'x' parameter) as there is only one "signal" detected per remitted structured light pattern. As a result, non-local information from spatially structured light waves, extending in the x-y plane, can be detected from measurement at a single spatial location. This capability derives from the phenomenon that the shape and magnitude of the reflected light wave at a single spatial location is a cumulative result of optical property-dependent multiple scattering within a volume that is typically larger than the single spatial point detection. Therefore the internal scattering tends to cause non-local or "global" effects on the structured light wave, typically resulting in a blurring or loss of contrast in the reflected structured light pattern. The lateral spatial scales of this blurring depend on the length scales of absorption and scattering in the medium, which can be much larger than the spot sampled by a single-element detector at the single spatial location. In this approach, two or more structured light projections give multiple "views" of the complex wave, allowing the non-local behavior of the waves to be detected by a single local measurement. Previously, this behavior was measured using a 20 camera covering a wide field of view in order to capture the spatially-dependent information in the x-y plane. As an example of this detection phenomenon, consider detecting a remitted peak or valley due to a sinusoidally-illuminated turbid medium in the form 1+cos(f/x). Due to the turbidity, the intensity measured at the specific peak or valley is a cumulative result of the internal properties extending laterally beyond multiple spatial periods away from the detection point. The "non-locality" of this sensing will depend on the relationship of the spatial period (1/fx) to the scales of light interaction within the medium (1/μa and 1/μs'). Put in another way, due the turbidity, a localized change or perturbation in optical properties (such as an increased absorption due to a tumor or blood vessel) will cause the remitted structured light pattern to be modified non-locally. In the above sinusoidal example, multiple peaks and crests will be modified as a result of a perturbation that is much smaller in extent than the spatial period of the light.

Analysis and/or reconstruction of single-point or single spatial location data would include one or more of the following steps:

1) signal conditioning of the measured data, such as signal averaging, filtering, normalization or background subtraction, to reduce the impact of undesired artifacts, such as noise or background signals;

2) isolation of an amplitude or phase component of the spatially-varying (AC) signal, such as:

a) demodulating the measured structured light signal due to a single spatial frequency of illumination to isolate the amplitude and/or phase of the spatially varying component to the reflected or transmitted wave, or b) performing the above where the spatially varying signal is instead composed of multiple spatial frequencies (a superposition of frequencies). Typically, this demodulation is done by combining data arising from multiple phase projections of the same structured light wave. Simple approaches to calculating amplitude or phase of the wave are discussed in Cuccia, *Quantitation and Mapping* and Bassi et al., *Spatial shift of spatially modulated light projected on turbid media*, J. Opt.

Soc. Am. A. 25(11) 2833 (2008)("Bassi, *Spatial Shift*"), which is incorporated by reference. One way is to combine the data to obtain amplitude data as follows:

$$AC\ amplitude=[\nu'(\%)]\cdot\nu f([A-B]^2+[B-C]^2+[C-A]^2),$$

where A, B, and C are data points collected under illumination of a spatial sinusoid with a phase of 0, 120, and 240 degrees, respectively;

3) isolation of an amplitude component of the spatially-constant (DC) signal, such as a single measurement under constant (planar) illumination conditions or computing an average or mean of multiple phase projections. See, Bassi, *Spatial Shift*; Cuccia, *Quantitation and Mapping*;

4) normalization or calibration of the AC or DC signals above with respect to measurements on a sample with known optical properties (a calibration phantom);

5) determination of the optical properties (absorption, reduced scattering, anisotropy, fluorescence, etc) of the sample based on one or more AC or DC signals, for example via model-based analysis (e.g. analytic, stochastic, or finite-element solvers), comparisons to previously-acquired data (e.g. measurements of phantom samples of known optical properties), or other heuristic approaches;

6) the above calculation in 5) where the computation can be performed via a look-up table of a-priori tabulated results;

7) determination of the depths of structures within the sample, for example via ratios or differences of AC and/or DC signals, model-based analysis (e.g. multi-layer or inclusion-based solvers), or other heuristic approaches;

8) combination of 5) or 6) with 7) to obtain sample depth and optical property determination such that an optical property can be assigned to a specific region;

9) use of bulk or region-wise optical properties at one or more wavelengths to determine the concentration or cross-section, and/or location of a particular material, dye, chromophore, etc.;

10) combination of metrics in 9) to provide simple indices that inform on the health, composition or other state of the sample;

11) comparison of a collection of data calculations in 1-10 obtained via various regions of the sample, multiple measurements of the same site, multiple wavelengths from the same site, multiple sites, multiple specimens or people, and/or multiple times in order to assess sample variation, compare one sample to a population, inform a therapeutic outcome, perform a diagnostic analysis, etc.

Figure 9:
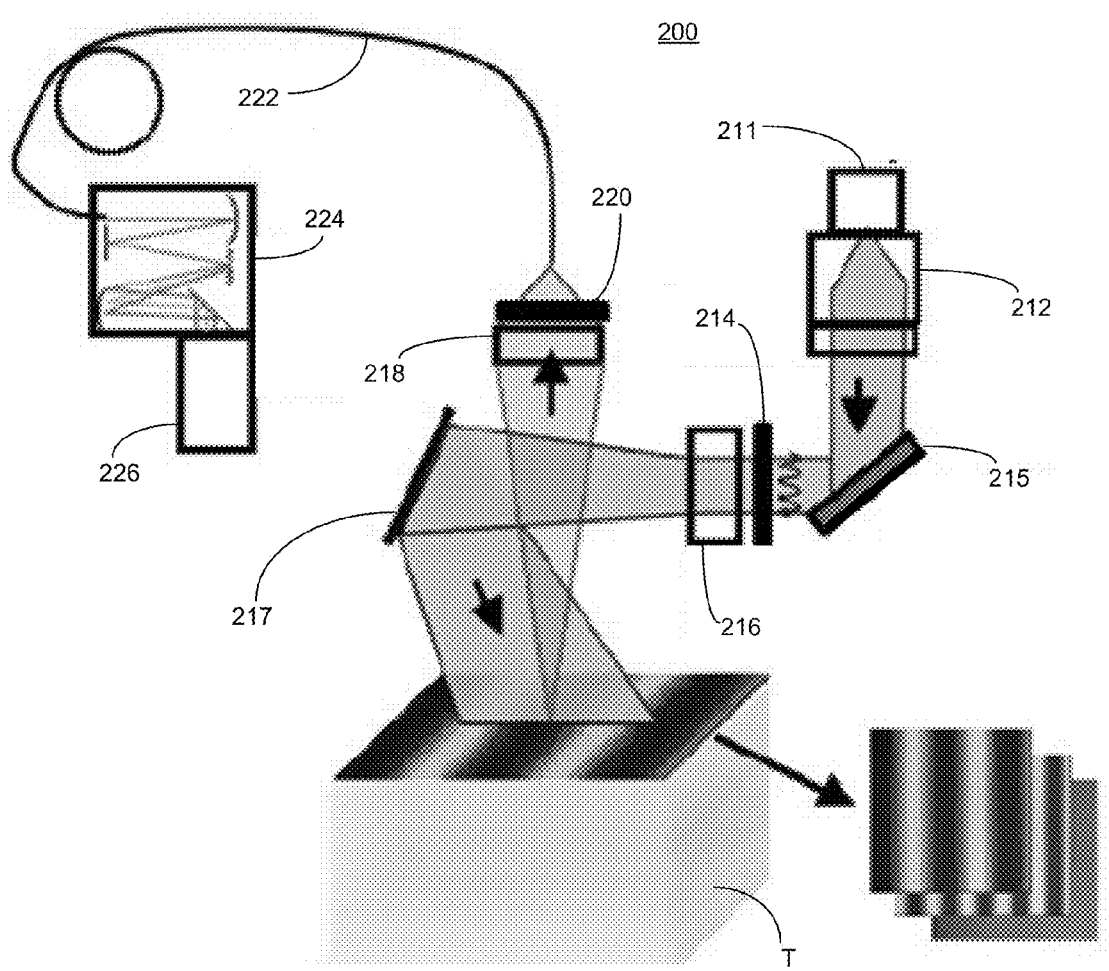
FIG. 9 is a schematic of a structured illumination system with a single element detector.

By making structured light measurements with a single element sensor (or otherwise detecting light remitting or transmitting from a single point or spatial location on the sample), the complexity of a 2D sensor detection is eliminated. This generally leads to three major practical advantages:

1. the core instrument can be potentially smaller, more sensitive, lower-noise, better intensity resolution, less expensive, and/or operate at lower power;
2. other measurement multiplexing approaches become more feasible, such as spectral multiplexing (via a spectrometer or detector array, for example), and polarization multiplexing; and
3. combination with other measurement approaches such as time-based measurements, or time-domain and time-frequency-domain photon migration techniques Turning to FIG. 9, a schematic of an example of a structured illumination system 200 with a single element detector is shown. As depicted, the system 200 includes a near infrared digital projector 210 comprising a broadband projection illumination source 211. Light from the illumination source 211 is delivered to a digital micro-mirror device (DMD) 215 via an integrating rod-based "light engine" 212 such as those provided in OLP projectors. The light from the DMD 215 is then imaged on to the surface of the target medium T, resulting in a projection field of view, e.g., a field of view of 50×68 mm. Collection optics (lens) 218 capture light remitted from a 2 mm diameter center subsection of the illuminated region. As depicted, these optics 218 couple light collected from this region to the distal tip of a 400 micron detector fiber 222. The light remitted from the sample is then delivered to a tunable spectrograph 224, tuned to a wavelength range and resolution, e.g., a wavelength range of 430-1050 nm, with a resolution of ~1 nm. A 16-bit CCD 226 acts as the detector. A crossed 2-inch diameter wire-grid polarizing filters 214 can be used to reject specular reflection from the surface of the sample. The polarizer 214 is inserted between the DMD 215 and projection optics 216 and the analyzer 220 is placed between the fiber 222 and collection optics 218.

As described below, the system 200 can be utilized in a non-contact method for the determination of quantitative optical properties of turbid medium, which is referred to hereafter as spatially modulated quantitative spectroscopy (SMoQS). Through measuring the broadband reflectance from an unknown sample as a function of the spatial frequency of the projected illumination patterns, the absolute absorption and reduced scattering coefficients can be calculated without a priori assumptions of the chromophores present.

Figure 10:
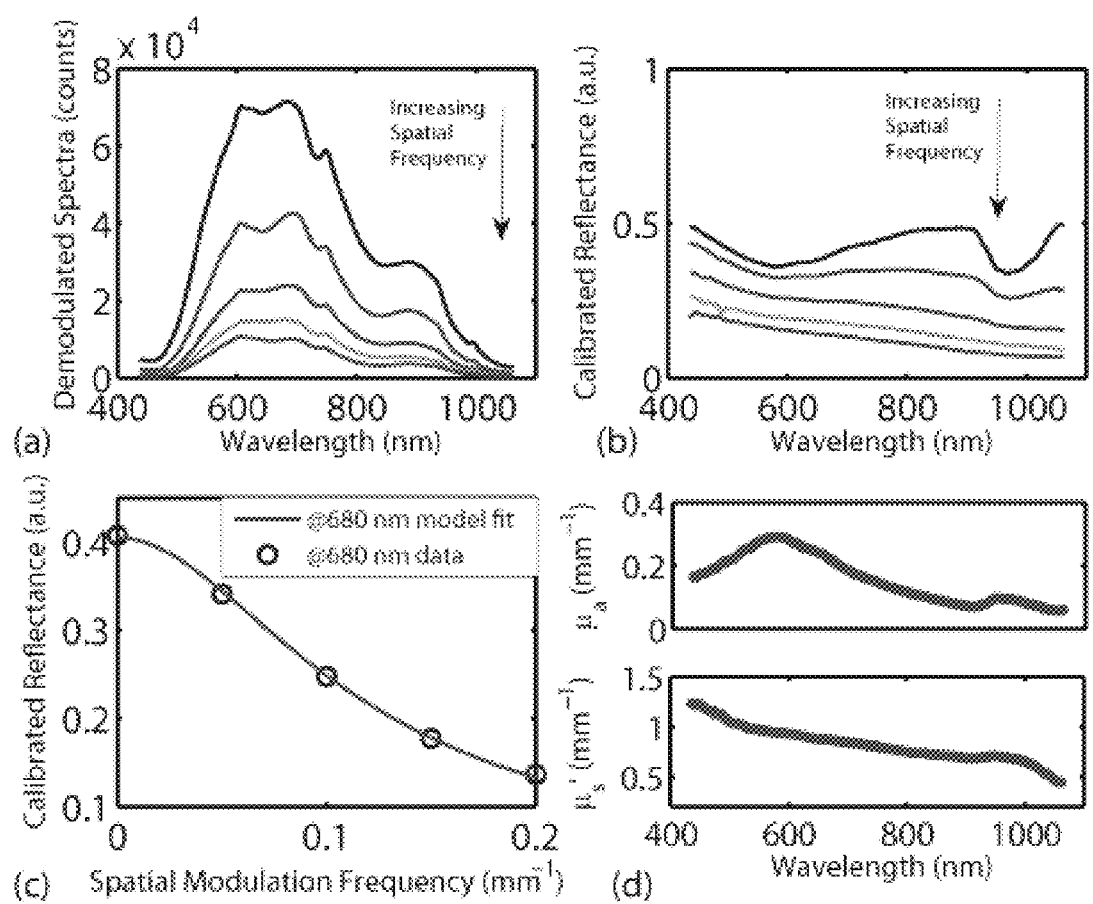
FIGS. 10(a)-10(d) are plots showing (a) an example of raw demodulated spectra, MAc(A-,fx), collected from a tissue simulating liquid phantom containing nigrosin, intralipid and water; (b) reflectance calibrated by the reference phantom measurement; (c) the diffuse "MTF," shown at 680 nm in this example, and (d) the resultant absorption and reduced scattering spectra.

For all samples measured in a SMoQS investigation utilizing the system 200, 15 illumination patterns based on two-dimensional sinusoids similar to that illustrated in FIG. 10(*a*) were used to characterize the samples. The spatial frequency of patterns spanned from 0 to 0.2 mm$^{-1}$ in steps of 0.05 mm$^{-1}$. Using a modulation/demodulation scheme that has been described by Cuccia, *Quantitation and mapping* each specific spatial frequency was projected 3 times, each with a phase shift of 0, 120 and 240 degrees. Data was acquired three times for each projected phase in order to further reduce noise. The raw spectral data were stored for each projection pattern and each phase. A reference calibration measurement was acquired from a liquid reference sample having known optical properties. This step is used to characterize the inherent MTF of the instrument.

Instead of measuring sequences of reflectance from a single wavelength across multiple pixels, in the SMoQS method, the entire broadband reflectance is measured for a single spatial location. This particular approach allows for a far greater wavelength range to be measured, however it is at the expense of imaging capabilities. In this case a full broadband spectrum is collected for every spatial frequency and phase. The broadband reflectance is then demodulated to extract the AC component of the detected light:

$$M_{AC}(\lambda, f_x) = \frac{\sqrt{2}}{3}\{[I_1(\lambda, f_x) - I_2(\lambda, f_x)]^2 + [I_2(\lambda, f_x) - I_3(\lambda, f_x)]^2 + [I_3(\lambda, f_x) - I_1(\lambda, f_x)]^2\}^{1/2} \quad (1)$$

resulting in the broadband AC reflectance for a given sample as a function of spatial frequency (FIG. 10(*a*)). Here, h(Jc Jx) denotes the measured reflectance spectrum at the three projected phases, i=[1,2,3]. Through the use of a reference phantom having known optical properties, the data can be calibrated and be given units of absolute reflectance (FIG. 10(*b*)). Here the highest trace corresponds to data acquired at a spatial frequency of 0/mm (i.e. planar illumination) and the lowest corresponds to data acquired at a spatial frequency of 0.2/mm. As the spatial frequency increases, the absorption band, which appears as a dip in the reflectance spectrum at 980 nm, becomes less apparent. This is in agreement with observations of decreasing absorption contrast with increasing spatial frequency as reported by Cuccia, *Quantitation and mapping*. At each wavelength, the reduction in AC reflectance amplitude as a function of spatial frequency (i.e. the effective MTF) can then be modeled and analyzed via Monte Carlo-based simulations (FIG. 10(c)) via discrete Hankel transformation of point-source reflectance predictions Cuccia, *Quantitation and mapping*. From this model, the contributions of absorption and scattering can be identified at each wavelength independently, resulting in broadband spectra for absorption and scattering without the use of any spectral constraints or an assumed power-law dependence for reduced scattering (FIG. 10d). Unlike diffusion-based models, this approach is not limited by albedo or frequency range. For modeling purposes, we assumed an anisotropy (g) value of 0.7 for the intralipid phantoms and 0.9 for skin. To demonstrate SMoQS' ability to accurately recover optical properties, a series of homogeneous liquid phantoms was prepared. Since it has been well characterized in terms of optical properties, Intralipid® (20%, Fresenius Kabi) was used as the scattering agent within the phantom. (H. J van Staveren et. al, *Light scattering in Intralipid-10% in the wavelength range of 400-1100 nm*, Applied Optics 30(31), 4507-4514(1991)(van Staveren)).

For these studies, multi-distance FDPM measurements (R. C. Haskell et al., *Boundary Conditions for the Diffusion Equation in Radiative Transfer*, Journal of the Optical Society of America-A, 10, 1-15, (1994)) were also performed to validate these values within 650-850 nm, independently confirming that the prepared phantoms match the expected scattering values that were determined analytically using the method proposed by van Staveren.

For simplicity and experimental control, a single dye was used as the primary absorbing agent in the liquid phantom. In this initial investigation, water-soluble nigrosin (Sigma Aldrich) was chosen as the absorber due to its broad spectral profile over the wavelength range of interest, allowing for a large dynamic range of absorption values to be measured in a single phantom. Moreover, the distributions of these values grossly mimic distributions that might be encountered in tissue—namely a broad absorption peak in the visible and low absorption in the near infrared. The spectral line shape and quantitative absorption values of each nigrosin solution, was measured, in the specific concentrations used in the liquid phantoms without any scatterer present, and confirmed using a spectrophotometer (Shimadzu UV-3600) over the entire wavelength range of interest.

Three phantoms were made, each designed with unique sets of optical properties. Two of these were treated as investigational samples. The first of these was a high albedo phantom, designed to have absorption and reduced scattering values ranges of [0.01-0.1] and [1.0-2.0] mm$^{-1}$, respectively, whereas the second phantom had a low albedo with absorption between [0.1-0.3] mm$^{-1}$ and reduced scattering in the range [0.5-1.2] mm$^{-1}$. These ranges extend well beyond expected values in the NIR, though remain conservative relative to values expected in the visible regime. The optical properties of the third phantom were chosen to fall between those of the two test phantoms, $\mu_a$=[0.1-0.3] and $\mu_s'$=[1.0-2.0]. This was used as a reference calibration to characterize the system MTF and spectral throughput.

Figure 11:
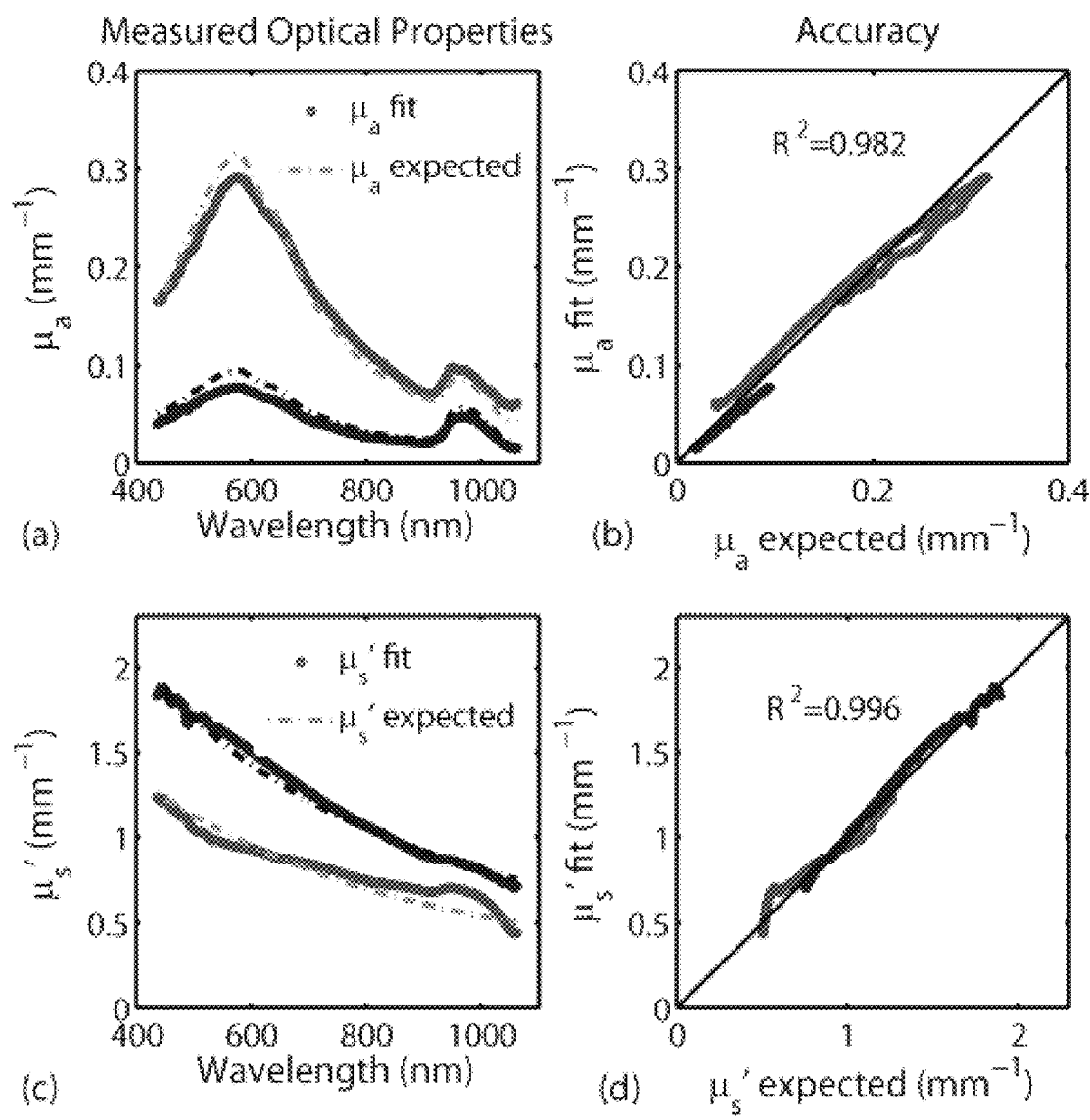
FIGS. 11(a)-11(d) are plots showing optical properties of high and low albedo phantoms including (a) measured and expected absorption spectra, (b) accuracy between expected and measured absorption values, (c) measured and expected reduced scattering spectra, and (d) accuracy between expected and measured reduced scattering.

FIG. 11 shows the extracted optical properties for the two liquid phantoms. In FIG. 11(a), the recovered absorption spectra for the low and high albedo phantoms are plotted along with the known concentrations of nigrosin and water used in the preparation of the phantoms. These absorption values were determined by the SMoQS method at each wavelength independently, yet faithfully produce the expected spectra, even in spectral regions where the source illumination and system throughput were weak, (i.e. 430-500 nm and 1000-1050 nm). Similar results were produced for the quantitative determination of reduced scattering coefficient (FIG. 11(c)). The recovery of optical properties was also successful as a function of the magnitudes of the expected values (FIGS. 11(b), 11(d)). This technique demonstrates a highly linear response across the range expected optical properties tested, resulting in R-Square values of 0.985 and 0.996 for absorption and scattering, respectively.

Figure 12:
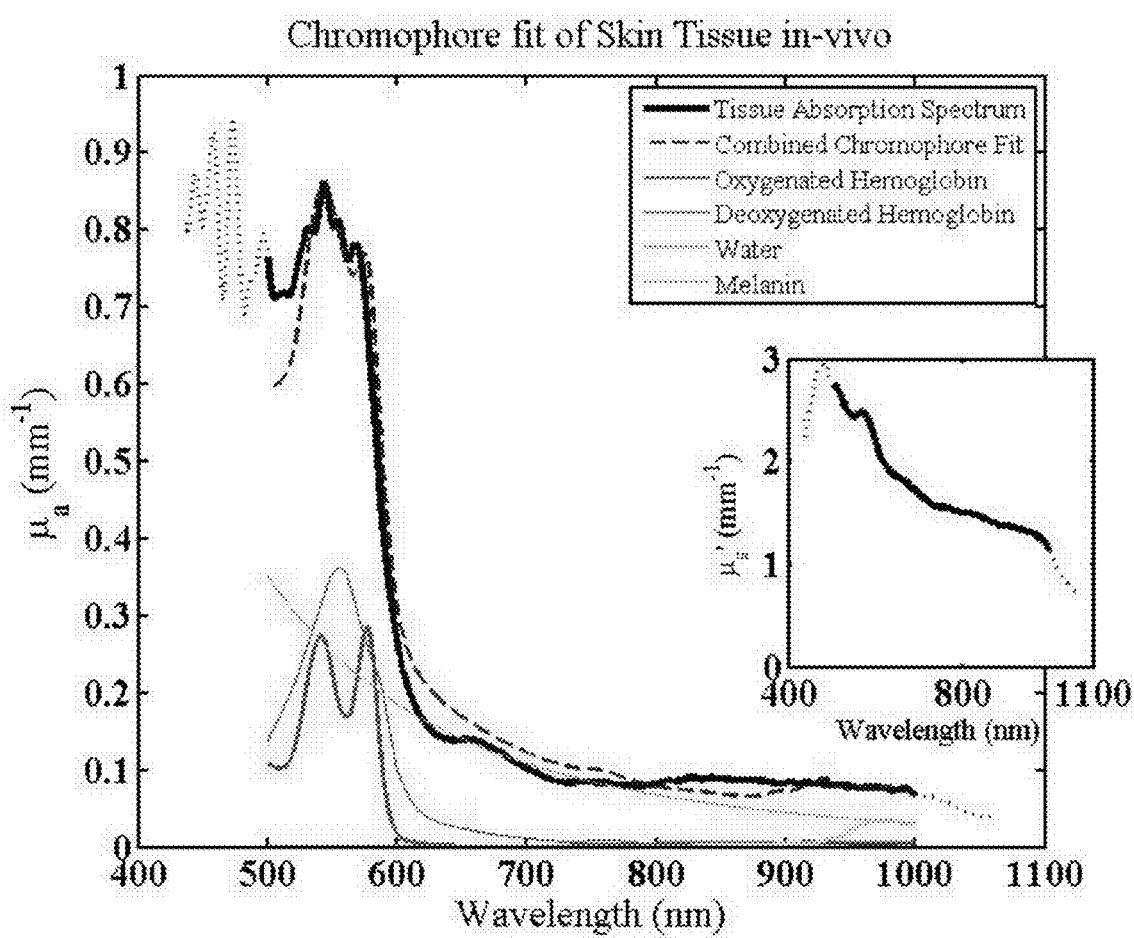
FIG. 12 is a plot showing measured absorption spectrum from the volar forearm and a subplot displaying the corresponding reduced scattering spectrum for this particular measurement.

For demonstration of basic feasibility, a measurement on in-vivo human tissue was also collected. In this particular case, a subject's volar forearm was placed under the projection illumination and light was specifically collected from a region of tissue that contained a large vein (IRB study protocol #1996-200). Using the same reference phantom that was employed in the liquid phantom experiment, absorption and reduced scattering spectra were extracted, shown in FIG. 12. The absorption spectrum was then fit in a linear least-squares sense to a basis set of spectra that included oxy- and deoxy-hemoglobin, water and melanin. Since the signal to noise of the system was particularly weak (<1) at the spectral limits of this measurement, this fit was only performed over a range of 500-1000 nm. The measured spectrum of skin was qualitatively well described by these physiologically relevant chromophores. The resulting quantitative contribution of each specific chromophore is in agreement with typical values for this type of tissue. These fits produced concentration values for oxy- and deoxy-hemoglobin of 22.4 and 28.4 μM, which are within ranges of values cited elsewhere for skin. (M. Kobayashi et al., *Analysis of nonlinear relation for skin hemoglobin imaging*, Optics Express 9(13) 802-812 (2001)). Additionally, it was determined that 70.2% of the volume probed comprised of water and 0.51% was melanin. (I. Nishidate et al., *Estimation of melanin and hemoglobin in skin tissue using multiple regression analysis aided by Monte Carlo simulation*, Journal of Biomedical Optics 9(4) 700-710 (2004)). Whereas is it acknowledged that skin is not a homogeneous medium and that the distribution of chromophores are depth selective, to first approximation, these results remain encouraging and opportunities remain for further layer-based modeling of SMoQS. (J. R. Weber et al., *Non-contact imaging of absorption and scattering in layered tissue using spatially-modulated structured light*, Journal of Applied Physics, 105, 102028 (2009)).

A new embodiment of spatial frequency domain (SFD) sampling in turbid media has been provided that is capable of characterizing optical properties over the range 430 to 1050 nm, with 1.5 nm resolution. Utilizing a SFD platform for quantitative spectroscopy is attractive not only for its ability to characterize turbid media across a very broad range of wavelengths, but the requisite instrumentation is relatively low in cost, non-contact, and simple to implement. The inherent flexibility of this approach allows for the tuning of the system for targeting specific wavelength regimes, permitting it to be used in a wide range of initial investigations. With the addition of scanning optics at the detection fiber, mapping of optical properties can be performed over entire region of tissue illuminated by the projected patterns. Spectral preconditioning of the source illumination would also help balance the dynamic range of detected, wavelength dependent reflectance, allowing for improved SNR in both spectral regions where absorption is characteristically strong as well as compensating for limitations in the spectral dependence in the systemic instrument function.

The in-vivo demonstration of the technique provides compelling evidence that the extracted absorption spectrum is well described by typical chromophores present in skin tissue. This analysis however was performed using a model that assumes that chromophores are homogeneously distributed in tissue. In reality, skin is heterogeneous on the scale of the interrogation volume of the device used here. Tissue interrogation over broad wavelength range will provide depth-dependent contrast to tissue chromophore species and structures, ranging from sub-millimeter probing depths in the visible to depth-sensitivity of many millimeters in the near infrared. Further investigation and modeling of this differential volume effect will be necessary prior to claims of robust quantitation of optical properties in layered media. (J. R. Weber).

The initial measurements described herein illustrate the basic capabilities of SMoQS as technique for quantifying optical properties in both visible and near infrared. It is able to characterize these optical properties without any a priori assumption and perform these measurements in a non-contact paradigm conducive to in-vivo characterization of tissue.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

The invention claimed is:

1. An apparatus for determining surface or subsurface optical properties or structures of a sample of turbid media over an area of the sample comprising:
    a source to expose an area of the sample to a structured illumination having a plurality of spatial features comprising one or more peaks and one or more valleys;
    one or more detection systems comprising an optical relay device and a detector coupled to the optical relay device, wherein the one or more detection systems are configured to collect an optical signal with no spatial dependence emitted from a first collection area at a first spatial location and a second collection area at a second spatial location on the surface of the sample within the area of the sample exposed to the structured illumination, wherein the second spatial location is spatially diverse from the first spatial location, the first and second collection areas at the first and second spatial locations being smaller in size than the area of the sample exposed to the structured illumination and having a dimension less than or equal to the length of an individual spatial feature of the plurality of spatial features of the structured illumination that illuminated the sample; and
    a signal processor coupled to the one or more detection systems and configured to reconstruct optical data from an individual optical signal with no spatial dependence collected from each of the first and second collection areas at the first and second spatial locations by the one or more detection systems and corresponding to the structured illumination.

2. The apparatus of claim 1 wherein the one or more detection systems further comprise a spectrograph optically coupled between the optical relay device and the detector.

3. The apparatus of claim 1 wherein the one or more detection systems comprise first and second spatially diverse detection systems configured to collect remitted light signals from the first and second collection areas at the first and second spatially diverse locations.

4. The apparatus of claim 1 wherein the optical relay device of the one or more detection systems is one of an optical fiber and a lens relay system.

5. The apparatus of claim 3 wherein the optical relay device of the first detection systems is one of an optical fiber and a lens relay system.

6. The apparatus of claim 1 wherein the one or more detection systems comprise a single detection system moveable between first and second spatially diverse locations and configured to collect remitted light signals from the first and second collection areas at the first and second spatially diverse locations on the surface of the sample within the area of the sample exposed to the structured illumination.

7. A method of determining surface or subsurface optical properties or structures of a sample of turbid media over an area of the sample comprising:
    exposing an area of the sample to a structured illumination having a plurality of spatial features comprising one or more peaks and one or more valleys;
    collecting an individual optical signal with no spatial dependence emitted from the sample by collecting optical signals with a detection system configured to collect optical signals from first and second collection areas, respectively, at first and second spatially diverse locations on the surface of the sample within the area of the sample exposed to the structured illumination, wherein the first and second collection areas being smaller in size than the area of the sample exposed to the structured illumination and having a dimension less than or equal to the length of an individual spatial feature of the plurality of spatial features of the structured illumination that illuminated the sample; and
    reconstructing optical data from the individual optical signals with no spatial dependence collected from the first and second collection areas at the first and second spatial locations and corresponding to the structured illumination.

8. The method of claim 7 wherein the step of collecting optical signals from the first and second collection areas at the first and second spatial locations on the surface of the sample includes collecting optical signals with one or more detection systems from the first and second collection areas at the first and second spatially diverse locations on the surface of the sample when the area of the sample is exposed to the structured illumination.

9. The method of claim 7 wherein the structured illumination is a spatially structured light wave extending over the surface of the sample.

10. The method of claim 9 wherein the step of reconstructing includes reconstructing optical data from a remitted structured light wave extending over the surface of the sample from the individual optical signals with no spatial dependence collected by one or more detection systems from the first and second collection areas at the first and second spatial locations on the surface of the sample.

11. The method of claim 8 wherein the one or more detection systems include an optical relay device and a detector optically coupled to the optically relay device.

12. The method of claim 11 wherein the optical relay device is one of an optical fiber and a lens relay system.

13. The method of claim 11 wherein the one or more detection systems further comprise a spectrograph optically coupled between the optical relay device and the detector.

14. The method of claim 13 wherein the detector is a CCD.

15. The method of claim 11 wherein the one or more detection systems further comprise collection optics optically coupled to the optical relay device.

16. The apparatus of claim 2 wherein the detector is a CCD.

17. The apparatus of claim 1 wherein the one or more detection systems further comprise collection optics optically coupled to the optical relay device.

18. The apparatus of claim 1 wherein the signal processor is a computer.

19. An apparatus for determining surface or subsurface optical properties or structures of a sample of turbid media over an area of the sample comprising:
- a source to expose an area of the sample to one or more structured illuminations having a plurality of spatial features comprising one or more peaks and one or more valleys;
- a detection system configured to collect optical signals with no spatial dependence emitted from first and second collection areas, respectively, at first and second spatially diverse locations on the surface of the sample within the area of the sample exposed to individual one of the one or more structured illuminations, and
- a signal processor coupled to the detection system and configured to reconstruct optical data from an individual optical signal with no spatial dependence collected from each of the first and second collection areas at the first and second spatial locations and corresponding to an individual one of the one or more structured illuminations, wherein the first and second collection areas being smaller in size than the area of the sample exposed to the one or more structured illuminations and having a dimension less than or equal to the length of an individual spatial feature of the plurality of spatial features of the individual one of the one or more structured illuminations that illuminated the sample.

20. The apparatus of claim 19 further comprising a second detection system spatially diverse from the detection system, wherein the detection system and the second detection system are configured to collect a single optical signal with no spatial dependence emitted from the first and second collection areas at the first and second spatially diverse locations on the surface of the sample when the area of the sample is exposed to the individual one of the one or more structured illuminations.

21. The apparatus of claim 20 wherein the detection system includes an optical relay device and a detector optically coupled to the optical relay device.

22. The apparatus of claim 21 wherein the detection system further comprises a spectrograph positioned between the optical relay device and the detector.

23. The apparatus of claim 22 wherein the detector comprises a CCD.

24. The apparatus of claim 21 wherein the optical relay device is one of an optical fiber and lens relay system.

* * * * *